United States Patent [19]

El Chahawi et al.

[11] 4,060,690

[45] Nov. 29, 1977

[54] METHOD OF PREPARING ARYLACETIC ACID ALKYL ESTERS

[75] Inventors: Moustafa El Chahawi, Troisdorf; Hermann Richtzenhain, Much-Schwellenbach, both of Germany

[73] Assignee: Dynamit Nobel Aktiengesellschaft, Troisdorf, Germany

[21] Appl. No.: 671,896

[22] Filed: Mar. 29, 1976

Related U.S. Application Data

[62] Division of Ser. No. 387,268, Aug. 10, 1973, Pat. No. 3,974,202.

[30] Foreign Application Priority Data

Aug. 17, 1972 Germany .............................. 2240399
Aug. 17, 1972 Germany .............................. 2240398

[51] Int. Cl.² .................. C07C 67/36; C07C 69/76
[52] U.S. Cl. ...................... 560/55; 560/100; 560/105

[58] Field of Search .................... 260/469, 476, 473 R

[56] References Cited

U.S. PATENT DOCUMENTS 3,009,951 11/1961 Kroeper et al. ................. 260/476 R
3,116,306 12/1963 Heck ................................ 260/476 R

*Primary Examiner*—Jane S. Myers
*Attorney, Agent, or Firm*—Burgess, Dinklage & Sprung

[57] ABSTRACT

In a process of producing an alkyl ester of a substituted or unsubstituted arylacetic acid wherein a substituted or unsubstituted aromatic halogen methyl compound is reacted with carbon monoxide and an alcohol having an alkoxy group the same as that of said ester, the improvement which comprises carrying out said reaction in a basic reaction medium in the presence as catalyst of:

a. cobalt salt, metal or metal alloy and a sulfur compound, or b. a metal carbonyl compound.

6 Claims, No Drawings

METHOD OF PREPARING ARYLACETIC ACID ALKYL ESTERS

This is a division, of application Ser. No. 387,268, filed Aug. 10, 1973, now U.S. Pat. No. 3,974,202.

THE BACKGROUND

The present invention relates to a method of preparing arylacetic acid alkyl esters.

Several processes are known for the preparation of phenylacetic acid esters. Thus, phenylacetic acid esters may be obtained through the reaction of benzyl chloride with alkali cyanide followed by saponification of the nitrile to the acid, and subsequent esterification (Ullmann, 1953, Vol. 4,291). What is unsatisfactory in this process is the plurality of steps in the reaction. Phenylacetic acid esters may also be obtained through the carbonylization of benzyl halides with the sodium salt of cobalt octacarbonyl (R. F. Heck et al., J. Amer. Chem. Soc. 85, (1963) 2779–82, and French Patent No. 1,313,306 of 1962). The use of the sodium cobalt carbonyl is extremely difficult technically and also provides poor yields. Phenylacetic acid esters are also accessible via the carbonylization of benzyl halides with CO under pressure in the presence of rhodium complexes (K. Ohno et al., J. Amer. Chem. Soc. 90, (1968) 99–107). Again, poor yields are obtained by this process, which has to be performed at higher pressures (100 atm.).

According to a new method of preparing phenylacetic acid esters, benzyl chloride is brought to reaction in polar solvents such as dimethyl formamide or dimethyl sulfoxide with carbon monoxide and alcohol in the presence of nickel tetracarbonyl and iodine as catalyst and in the presence of alkaline earth oxides as HCl acceptors (German "Offenlegungsschrift" 1,914,391). The disadvantages of this process result from the large amounts of nickel carbonyl and iodine that are needed as catalysts, and from the recovery of the expensive solvents used. On the basis of the long reaction time of 26.5 hours poor unit-volume yields are obtained, which make the process uneconomical.

THE INVENTION

It has now been found that, through the catalytic reaction of an aromatic methyl chloride compound with carbon monoxide in the presence of a basic medium and the corresponding alcohols, the arylacetic acid ester can be obtained directly.

Surprisingly, under the reaction conditions applied, the benzyl alkyl ether is not formed, as might be expected, from benzyl chloride and sodium alcoholate, for example, and instead the reaction takes place in accordance with the following equation:

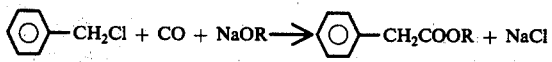

In this equation, R represents a saturated aliphatic alkyl radical with 1 to 6 carbon atoms.

By arylacetic acid alkyl esters are meant the unsubstituted phenylacetic acid alkyl esters as well as substituted phenylacetic acid alkyl esters, condensed aromatic rings being able to be present as aryl radicals and being able to bear one or more additional substituents, preferably chlorine, alkyl radicals with 1 to 6 carbon atoms or alkoxy radicals with 1 to 6 carbon atoms. Examples are mono-, di- and tetrachlorophenylacetic acid alkyl esters, monomethyl and dimethyl or monopropyl and dipropyl phenylacetic acid alkyl esters, mono- and dimethoxy or -ethoxyphenylacetic acid alkyl esters, naphthyl acetic acid methyl or ethyl esters, etc.

The starting materials are the structurally corresponding, unsubstituted aromatic halogen methyl compounds or those bearing the desired substituents, preferably the chloromethyl compounds.

The alcohols used and the alkyl radicals of the alkali alcoholates are those corresponding structurally to the radicals entering into the particular alkylester radicals of the phenylacetic acid alkyl esters, not only the primary but also secondary and tertiary alcohols or the corresponding alcoholates being able to be used.

The carbon monoxide pressure may be 0.1 to 25 atmospheres, preferably 0.1 to 10 atmospheres excess pressure.

The catalyst (a) may be a catalyst system consisting of three components, namely a cobalt salt such as cobalt halide, cobalt acetate, cobalt-II-acetylacetonate, cobalt nitrate and cobalt-II-hydroxide-carbonate; metallic manganese, iron, nickel or alloys thereof such as iron-manganese alloys in finely divided form, a water-soluble sulfur compound such as sodium dithionite, sulfoxylates (Rongalite) or sodium sulfide-sodium thiosulfate.

The reaction takes place at atmospheric or slightly higher pressure and leads to the desired arylacetic ester with a high yield.

For the preparation of the catalyst system, CO or a CO-containing gas mixture such as water gas is introduced into a solution of $CoCl_2 \cdot 6H_2O$ in alcohol, metal powder and $Na_2S_2O_4$ until no more appreciable amounts of CO are absorbed. The introduction of the CO takes place at 10° to 100°, preferably 20° to 40° C, and continues for about 30 minutes. Then, at a temperature between 30° and 80°, preferably 50° to 60° C, while the introduction of CO is continued and intensified, the aromatic chloromethyl compound and the alkali alcoholates or alkaline earth oxides preferred as the alkaline medium are added in such quantity ratio that the reaction medium always has an alkaline, preferably a weakly alkaline, reaction. It is desirable that the sodium alcoholate be added in the form of a 10 to 25 wt-% solution in alcohol. The aromatic chloromethyl compound may be added all at once to the catalyst mixture or it may be fed in continuously. The feeding of CO and alcoholate to the solution of the particular alcohol, or CaO with the particular alcohol, takes place for a period of about 3 to 5 hours. The introduction of CO is further continued until its absorption has stopped. As a rule this absorption will end about 3 hours after the addition of the components. As a rule, then, the total reaction time (including the preparation of the catalyst) will be 6 to 8 hours.

The molar ratio of basic reagent to aromatic methyl chloride compound is preferably around 1:1, although slight excesses of the basic substance may be used so that a weakly alkaline reaction will be maintained by a slight excess of the basic substance and an acid reaction will be avoided. A slow, constant or portion-wise addition of the basic substance during the reaction of the halogen methyl compound is therefore preferred.

The metal powder or alloy may be used in a particle size between 0.10 and 300 microns, preferably between 50 and 200 microns. The ratio by weight of the metal powder or alloy to the chloromethyl compound can best range between 1:1 and 1:1000, the upper limit being determined only by the ability of the reaction medium to be stirred. Preferably the ratio will be between 1:10 and 1:100.

The process of the invention permits both the isolation and the recovery of the metal powder or alloy. The weight ratio of the cobalt compound to the methyl chloride compound may range between 1:1 and 1:500, preferably 1:2 to 1:50. The sulfur compound is used in a small quantity, the weight ratio of the sulfur compound to the methyl chloride compound being between 1:3 and 1:1500, preferably between 1:30 and 1:500.

A metal carbonyl compound may also be used as catalyst (b), the cobalt and/or iron carbonyls being preferred.

The reaction takes place at atmospheric or slightly higher pressure and results in very high yields of the desired arylacetic ester. For the preparation of the said ester, iron carbonyl or cobalt carbonyl is placed in a saturated alcohol with 1 to 6 carbon atoms as the solvent and CO or a CO-containing gas mixture such as water gas is introduced. Then, at a temperature between 10° and 100° C, preferably 50° to 60° C, with the continued introduction of CO, the substituted or unsubstituted aromatic chloromethyl compound that is to be carbonylized, and a sodium alcoholate of a saturated aliphatic, primary, secondary or tertiary alcohol of 1 to 6 carbon atoms are added in such a quantity ratio that the reaction medium will always have an alkaline, preferably weakly alkaline, reaction. The substituted or unsubstituted aromatic methyl chloride to be carbonylized, however, may also be added all at once at the beginning of the reaction. It is desirable that sodium alcholate be added in the form of a 10 to 30 wt-% solution in alcohol.

The catalyst may likewise be added all at once to the reaction solution or it may be fed into it continuously. The introduction of carbon monoxide is continued until absorption ceases. As a rule such absorption will have ceased about 3 to 8 hours after the addition of the components.

The quantity ratio of basic reagent to the aromatic methyl chloride compound is preferably 1:1, although slight excesses of the basic substance may be used so that a weakly alkaline reaction will be maintained by a slight excess of the basic substance and an acid reaction will be avoided.

The weight ratio of metal carbonyl to the methyl chloride compound may be between 1:1 and 1:500, preferably 1:20 to 1:200.

The processing of the reaction batch is particularly simple inasmuch as the solid components (sodium chloride, metal powder) are simply separated by filtration. Water may be added to the filtrate, whereupon the reaction product separates in fairly pure form as an organic phase. The aqueous phase consists of a mixture of alcohol and water which contains dissolved therein the cobalt compound and the sulfur compound and the sodium salt of the arylacetic acid formed as by-product.

The filtrate may also be distilled directly, leaving small amounts of sodium chloride and of the metal carbonyls used.

The phenylacetic esters prepared by the process of the invention find use as perfumes and are valuable chemical intermediates.

EXAMPLE 1

To 100 ml of methanol were added 12 g of $CoCl_2.6 H_2O$, 6 g of powdered manganese (150 μ) and 1 g of sodium dithionite, in a carbon monoxide atmosphere. Carbon monoxide was then passed through the mixture with stirring (500 rpm), for 30 minutes at 35° C, with an overpressure of 600 mm Hg. Then the mixture was heated to 55° C and, over a period of 3 hours, 190 g (1.5 moles) of benzyl chloride and 404 g (1.5 moles) of 21 wt-% sodium methylate solution were added while constantly feeding in carbon monoxide and at a stirring speed of 500 to 750 rpm.

Carbon monoxide continued to be introduced for about 2½ more hours, until no more absorption took place. Then the sodium chloride and manganese were separated, water was added to the filtrate, and the filtrate was extracted with ether. After distillation of the ether, a reaction mixture remained from which 170 g of phenylacetic acid methyl ester (yield 78%, purity 99.7%) and 6.9 g of benzyl chloride were isolated by distillation.

After acidification of the aqueous phase and extraction with ether, an additional 18 g of phenylacetic acid was isolated (yield 9.1%, purity 99.3%).

EXAMPLE 2

In the manner described in Example 1, 300 g of benzyl chloride, 620 ml of 21 wt-% sodium methylate and, as catalysts, 20 g of $CoCl_2.6 H_2O$, 1 g $Na_2S$, 1.5 g $Na_2S_2O_3.5 H_2O$, and 9 g of powdered manganese, were reacted with carbon monoxide. After the described processing, the reaction mixture yielded 21 g benzyl chloride (93% transformation), 214 g of phenylacetic acid methyl ester (yield 64.7%) and 26 g of phenylacetic acid (yield 8.6%).

EXAMPLE 3

As described in Example 1, 190 g of benzyl chloride, 404 g of 21 wt-% sodium methylate and, as catalysts, 12 g $CoBr_2.6 H_2O$, 6 g manganese powder and 1 g $Na_2S_2O_4$, were reacted with carbon monoxide. 7 g of benzyl chloride, 125 g of phenylacetic acid methyl ester (yield 57.6%), 13.4 g of phenylacetic acid (yield 6.8%) and 23 g of methylbenzyl ether were isolated from the reaction mixture after the described processing.

EXAMPLE 4

As described in Example 1, 190 g of benzyl chloride, 404 g of 21 wt-% sodium methylate, 12 g of $Co(CH_3COO)_2.4 H_2O$, 6 g of powdered manganese and 1 g of $Na_2S_2O_4$ were reacted with CO. 2.9 g of benzyl chloride, 152 g of phenylacetic acid methyl ester (yield 68.5%), 5 g of phenylacetic acid (yield 2.5%) and 11 g of methylbenzyl ether (yield 6%) were isolated from the reaction mixture after the described processing.

EXAMPLE 5

As described in Example 1, 190 g of benzyl chloride, 100 g of calcium oxide, 750 ml of methanol, 6 g $CoCl_2.6 H_2O$, 6 g manganese powder and 3 g $Na_2S_2O_4$ were reacted with Co, the calcium oxide being added over a period of 3 hours. 10 g of benzyl chloride, 122 g phenylacetic acid methyl ester (yield 57%), 37 g phenylacetic acid (yield 19%) and 2 g methylbenzyl ether were isolated from the reaction mixture after the described processing.

EXAMPLE 6

As described in Example 1, 126.5 g of benzyl chloride, 270 g of 21 wt-% sodium methylate, 11 g $Co_2(CO)_8$, 4 g manganese and 1 g $Na_2S_2O_4$ were reacted with CO.

133.5 g of phenylacetic acid methyl ester (yield 89%) was isolated from the reaction mixture in a purity of 97.25%.

EXAMPLES 7 to 16

In the examples listed in the following table, 190 g of benzyl chloride (1.5 moles) were reacted in each case with CO in the presence of the specified catalysts. The basic agent in each case was 355 g of a 24 wt-% solution of sodium methylate in methanol.

TABLE I

| Ex. No. | Catalyst System | | | Dist. in g |
|---|---|---|---|---|
| | Metal | Cobalt compound | Sulphur compound | |
| 7 | 4 g Mn | 6 g $CoCl_2 \cdot 6H_2O$ | Rongalite 1 g | 185 |
| 8 | 6 g Ni | 12 g $CoCl_2 \cdot 6H_2O$ | $Na_2S_2O_4$ 1 g | 165 |
| 9 | 6 g Fe | 12 g $CoCl_2 \cdot 6H_2O$ | " | 160 |
| 10 | 4 g Mn+) 45 – 150 μ | 6 g $CoCl_2 \cdot 6H_2O$ | " | 200 |
| 11 | 6 g Mn | 12 g CoII-acetylacetonate | " | 192 |
| 12 | 6 g Mn | 12 g $CoI_2 \cdot 2H_2O$ | " | 200 |
| 13 | 6 g Mn+) 0.15 mm | 12 g $CoCl_2 \cdot 6H_2O$ | " | 184 |
| 14 | 6 g Mn++) 0.15 mm | 12 g $CoCl_2 \cdot 6H_2O$ | " | 180 |
| 15 | 6 g Mn | 12 g $Co(NO_3)_2 \cdot 6H_2O$ | " | 163.5 |
| 16 | 6 g Fe/Mn | 12 g $CoCl_2 \cdot 6H_2O$ | " | 160 |

+) = Thermally produced
++) = Electrolytically produced

TABLE II

| Example No. | Gas chromatogr. analysis of the distillate+++ | | | | |
|---|---|---|---|---|---|
| | $PhCH_2Cl$ | $PhCH_2OCH_3$ | $PhCH_2COOCH_3$ | $PhCH_2COOH$ | $PhCH_2COOCH_2Ph$ |
| 7 | 3.89 | 18.94 | 72.17 | 3.63 | 0.43 |
| 8 | 24.11 | 58.59 | 12.62 | 4.28 | — |
| 9 | 21.18 | 63.68 | 9.21 | 5.43 | — |
| 10 | 2.97 | 11.90 | 79.87 | 0.28 | 0.28 |
| 11 | 2.72 | 38.33 | 57.43 | 0.18 | 0.44 |
| 12 | 0.34 | 5.17 | 92.41 | 1.04 | 0.84 |
| 13 | 11.19 | 35.41 | 43.99 | 7.75 | 0.51 |
| 14 | 17.08 | 41.96 | 30.03 | 9.13 | 0.48 |
| 15 | 12.28 | 17.97 | 61.58 | 6.51 | 0.53 |
| 16 | 9.51 | 10.87 | 69.65 | 8.23 | 0.64 |

+++in wt-% with reference to the distllate
The chromatography column had a packing of Silicone Gum Rubber UCC W-982 (methyl vinyl)

EXAMPLE 17

Phenylacetic acid methyl ester 2.5 g $CoCl_2 \cdot 6H_2O$, 2 g manganese powder (150 μ) and 1 g $Na_2S_2O_4$ were added to 100 ml of methanol in a CO atmosphere. Then CO was passed through the mixture with stirring (500 rpm) at 35° C for 30 minutes with an overpressure of 600 mm Hg. At 55° C, 190 g of benzyl chloride was added to the reaction mixture. Then, over a period of 3 hours with the steady passage of CO, 355 g of 24 wt-% sodium methylate solution was fed in with a stirring speed of 500 to 750 rpm. Carbon monoxide was introduced for another 2½ hours, approximately, until no more absorption took place. Then water was added to the mixture and the latter was separated from the manganese. The mixture was extracted with ether. After the ether was removed by distillation there remained a reaction mixture from which 3.5 g of benzyl chloride and 189 g of phenylacetic acid methyl ester (yield 85.4%) were isolated by distillation.

After acidification of the aqueous phase and extraction with ether, it was possible to isolate an additional 5 grams of phenylacetic acid (yield 2.5%).

EXAMPLE 18 p-Chlorophenylacetic acid methyl ester

As described in Example 1, 80.5 g (0.5 mole) of p-chlorobenzyl chloride with 135 g of a 24 wt-% sodium methylate solution, 10 g of $CoCl_2 \cdot 6H_2O$, 4 g of manganese and 1 g of sodium dithionite were reacted with CO. The reaction and processing were performed as described in Example 1. 74 g of p-chlorophenylacetic acid methyl ester (yield 80%) was isolated in a purity of 96%, plus 4 g of p-chlorophenylacetic acid (4.6%).

EXAMPLE 19 p-Methylphenylacetic acid methyl ester

In the manner described in Example 1, 70.5 g (0.5 mole) of p-methylbenzyl chloride and 135 g of a 24 wt-% sodium methylate solution in methanol, 5 g $CoCl_2 \cdot 6 H_2O$, 4 g manganese powder and 1 g sodium dithionite were reacted with CO. The reaction and the processing were performed as described in Example 1. 47.0 g of p-methylphenylacetic acid methyl ester ($BP_{13}$ 113°) (yield 57.2%) was isolated in a purity of 98%, plus 6.2 of p-methylphenylacetic acid (MP 89°–90° C, yield 8%).

EXAMPLE 20

Naphthyl-(1)-acetic acid methyl ester

In the manner described in Example 1, 58 g of alpha-chloromethylnaphthalene was reacted with CO together with 78 g of a 24 wt-% sodium methylate solution in methanol, 12 g $CoCl_2 \cdot 6 H_2O$, 6 g manganese and 1 g $Na_2S_2O_4$. The usual processing yielded 35 g naphthyl-(1)-acetic acid methyl ester (yield 53%) and 7 g of alpha-naphthylacetic acid (yield 6.5%).

EXAMPLE 21 p-Methoxyphenylacetic acid methyl ester

In the manner described in Example 1, 50 g of p-methoxybenzyl chloride was reacted with CO together with 115 g of a 24 wt-% solution of sodium methylate in methanol, 12 g $CoCl_2 \cdot 6 H_2O$, 6 g manganese and 1 g $Na_2S_2O_4$. After distillation of the reaction mixture the following compounds could be identified by gas chromatography.

| p-methoxybenzyl chloride | 10.00% |
|---|---|
| p-methoxymethylbenzyl ether | 69.50% |
| p-methoxyphenylacetic acid methyl ester | 8.66% |
| p-methoxyphenylacetic acid | 5.54% |

EXAMPLE 22

Phenylacetic acid ethyl ester

In a manner similar to Example 17, 126.5 g of benzyl chloride, 794 g of a 9 wt-% solution of sodium ethylate in ethanol, 12 g CoCl$_2$.6 H$_2$O, 6 g manganese powder and 1 g Na$_2$S$_2$O$_4$ were reacted with CO. After the usual processing, 8 g of benzyl chloride, 109 g of phenylacetic acid ethyl ester (yield 71%), 8 g of phenylacetic acid (yield 6%) and 1 g of ethylbenzyl ether were isolated.

EXAMPLE 23

In a manner similar to Example 1, 63.5 g(½ mole) of benzyl chloride, 6 g CoCl$_2$.6 H$_2$O, 4 g manganese powder, 1 g Na$_2$S$_2$O$_4$ in 100 ml of tert. butanol and 56 g of potassium tertiary butylate were reacted with CO. The reaction and processing were performed as in Example 1.

55 g of reaction mixture was distilled, which on the basis of gas chromatography contained the following:

| | |
|---|---|
| Benzyl chloride | 18.6% |
| Phenylacetic acid tert. butyl ester | 79.18% |

EXAMPLE 24

In the manner described in Example 17, 190 g of benzyl chloride, 329 of 25.8 wt-% sodium methylate, 12 g of CoCl$_2$.6 H$_2$O, 6 g manganese powder and 1 g Na$_2$S$_2$O$_4$ were reacted with a mixture of carbon monoxide and hydrogen gas in a ratio of 3:1.

After distillation of the reaction mixture (180 g) the following results were obtained by gas chromatography:

| | |
|---|---|
| Benzyl chloride | 20.24% |
| Methylbenzyl ether | 25.43% |
| Phenylacetic acid methyl ester | 44.76% |
| Phenylacetic acid | 5.31% |

EXAMPLE 25

In the manner described in Example 1, 190 g of benzyl chloride together with 355 g of 24 wt-% NaOCH$_3$, 12 g of cobalt (II)hydroxide carbonate*, 6 g of manganese and 1 g of Na$_2$S$_2$O$_4$ were reacted with CO. 175.5 g was distilled which, according to GC, contained the following:

| | |
|---|---|
| Benzyl chloride | 10.43% |
| Methylbenzyl ether | 82.77% |
| Phenylacetic acid methyl ester | 6.1% |

* as commercial available from MERCK, Darmstadt (Germany)

EXAMPLE 26

6 g of cobalt octacarbonyl was added to 100 ml of methanol. Then CO was passed through with stirring (500 rpm) at 35° C for 30 minutes with an excess pressure of 600 mm Hg. Then the mixture was heated to 55° C and, with a steady feed-through of CO, 190 g (1.5 mole) of benzyl chloride and 329 g of 25.8 wt-% sodium methylate were fed in over a period of 3 hours at a stirring speed of 500 to 750 rpm. Carbon monoxide delivery continued for about 2½ more hours until no further absorption took place. Then water was mixed with the reaction mixture and it was extracted with ether. After distilling the ether a reaction mixture was obtained from which 215 g of phenylacetic acid methyl ester in a purity of 97.03% was obtained by distillation (yield 95.4%).

EXAMPLE 27

In the manner described in Example 26, 4 g of Co$_2$(CO)$_8$, dissolved in 100 ml of ethanol, 126.5 g of benzyl chloride and 794 g of 9 wt-% of NaOC$_2$H$_5$ dissolved in ethanol (H$_2$O content 0.17%) were reacted with CO. The reaction and the processing were performed as in Example 26. 136 g of reaction mixture was distilled, which according to gas-chromatographic analysis (GC) had the following composition:

2.37% ethylbenzyl ether
2.53% benzyl chloride
70.75% phenylacetic acid ethyl ester
13.79% phenylacetic acid.

EXAMPLE 28

In the manner described in Example 26, 3 g of Co$_2$(CO)$_8$, 80.5 g (0.5 mole) of p-chlorobenzyl chloride and 110 g of 25.8 wt-% sodium methylate were reacted with CO. The reaction and processing were performed as in Example 26. 6.5 g of p-chlorobenzylchloride and 76 g of p chlorophenylacetic acid methyl ester (yield 89.8%) were distilled in a purity of 97.75%.

EXAMPLE 29

In the manner described in Example 26, 4 g of Co$_2$(CO)$_8$, 70.5 g (0.5 mole) of p-methylbenzyl chloride and 110 g of 25.8 wt-% sodium methylate were reacted with CO. The reaction and the processing were performed as in Example 26. 2 grams of p-methylbenzyl chloride and 69 g of p-methylphenylacetic acid methyl ester (yield 86.7%) were distilled in a purity of 99.25%.

EXAMPLE 30

In the manner described in Example 26, 4 g of Co$_2$(CO)$_8$, 76 g (0.43 mole) of α-chloromethylnaphthalene and 95 g of sodium ethylate were reacted with CO. The reaction and processing were performed as in Example 26.

After the distillation of the reaction mixture (65 g), the following were determined by GC:

39.2% methoxymethylnaphthaline
3.03% chloromethylnaphthaline
54.27% naphthyl-(1)-acetic acid methyl ester.

EXAMPLE 31

In the manner described in Example 26, 4 g of Co$_2$(CO)$_8$, 57 g (0.36 mole) of p-methoxybenzyl chloride and 78 g of 25.8 wt-% sodium methylate were reacted with CO. After processing, 50 g were distilled. The following compounds were determined by GC:

30.8% p-methoxymethylbenzyl ether
24.76% p-methoxybenzyl chloride
40.93%, p-methoxyphenylacetic acid methyl ester.

EXAMPLE 32

In the manner described in Example 26, 9 ml of Fe(CO)$_5$, 190 g of benzyl chloride and 329 g of 25.8 wt-% sodium methylate were reacted with CO. The reaction and processing were performed as in Example 26. After distillation of the reaction mixture the following compounds were determined by GC:

6.03% benzyl chloride
55.76% methyl benzyl ether
34.07% phenylacetic acid methyl ester.

EXAMPLE 33

In the manner described in Example 26, 22 ml of $Fe(CO)_5$, 190 g of benzyl chloride and 329 g of 25.8 wt-% sodium methylate were reacted with CO. 175 grams of distillate were obtained with the following composition according to GC:

0.81% benzyl chloride
4.56% methylbenzyl ether
90.61% phenylacetic acid methyl ester.

EXAMPLE 34

In the manner described in Example 26, 6 g of $Co_2(CO)_8$, 190 g of benzyl chloride and 329 g of 25.8 wt-% sodium methylate were reacted with a $CO/H_2$ gas mixture in a 3:2 ratio. 173 g were distilled with the following composition:

4.92% benzyl chloride
63.52% methylbenzyl ether
25.91% phenylacetic acid methyl ester.

EXAMPLE 35

In the manner described in Example 26, 4 g of $Co_2(CO)_8$, 100 ml of methanol, 126.6 g (1 mole) of benzyl chloride and 56 g of CaO were reacted with CO. The reaction was performed as in Example 26. After that the mixture was acidified with hydrochloric acid and processed as in Example 26.

104 g of reaction mixture was distilled, which contained the following composition according to GC:

| Benzyl chloride | 32.83% |
| Phenylacetic acid methyl ester | 40.71% |
| Phenylacetic acid | 23.88% |

EXAMPLE 36

In the manner described in Example 26, 2.5 g of $Co_2(CO)_8$, 100 ml of tertiary butanol, 63.5 (½ mole) of benzyl chloride and 56 g of potassium-tertiary-butylate were reacted with CO. The reaction and processing were performed as in Example 26.

52 g of reaction mixture were distilled, which contained the following composition according to GC:

| Tertiary butanol | 11.16% |
| Benzyl chloride | 12.45% |
| Phenylacetic acid tert.-butyl ester | 74.18% |

EXAMPLE 37

By the procedure described in Example 26, 4 g of $Co_2(CO)_8$, 55 g of 4-isopropyl-1-chloromethylbenzene and 100 g of 25.8 wt-% sodium methylate were reacted with CO. After processing 47 g of p-isopropylphenylacetic acid methyl ester were isolated.

What is claimed is:

1. In a process of producing an alkyl ester of a substituted or unsubstituted arylacetic acid wherein a corresponding substituted or unsubstituted benzyl halide is reacted with carbon monoxide and an alcohol having an alkoxy group the same as that of said ester, the improvement which comprises carrying out said reaction in a basic reaction medium at a temperature of about 10°–100° C, and a carbon monoxide pressure of about 0.1–25 atmospheres in the presence as catalyst of at least one cobalt salt of the group cobalt halide, cobalt acetate, cobalt-acetylacetonate, cobalt nitrate, cobalthydroxide-carbonate and $Co_2(CO)_8$, at least one metal or metal alloy of the group manganese, iron, nickel and alloys thereof, and at least one water soluble sulfur compound of the group sodium dithionate, sulfoxylates, and sodium sulfide-sodium thiosulfate.

2. Process according to claim 1, wherein the catalyst is reacted with CO.

3. Process according to claim 1, wherein the catalyst is provided by combining the components thereof with the alcohol in the sequence cobalt salt, metal or metal alloy, sulfur compound.

4. Process according to claim 1, wherein at least one of an alkali alcoholate or an alkaline earth oxide is included in the reaction medium to render it basic.

5. Process according to claim 1, wherein carbon monoxide is added in admixture with another gas.

6. Process according to claim 1, the metal or alloy being manganese or an alloy thereof.

* * * * *

UNITED STATES PATENT AND TRADEMARK OFFICE
CERTIFICATE OF CORRECTION

PATENT NO. : 4,060,690
DATED : November 29, 1977
INVENTOR(S) : Moustafa El Chahawi and Hermann Richtzenhain It is certified that error appears in the above—identified patent and that said Letters Patent are hereby corrected as shown below:

Column 9, line 50, insert "g" after 63.5

Signed and Sealed this

Seventh Day of March 1978

[SEAL]

Attest:

RUTH C. MASON
Attesting Officer

LUTRELLE F. PARKER
Acting Commissioner of Patents and Trademarks